US006225452B1

(12) United States Patent
Levin

(10) Patent No.: US 6,225,452 B1
(45) Date of Patent: May 1, 2001

(54) INCREASED FERTILITY AND IMPROVED FETAL DEVELOPMENT DRUG

(75) Inventor: Gilbert V. Levin, Annapolis, MD (US)

(73) Assignee: Biospherics Incorporated, Beltsville, MD (US)

( * ) Notice: Subject to any disclaimer, the term of this patent is extended or adjusted under 35 U.S.C. 154(b) by 0 days.

(21) Appl. No.: 09/299,026

(22) Filed: Apr. 26, 1999

(51) Int. Cl.[7] .............................. A61K 31/70; C07H 1/00
(52) U.S. Cl. ........................... 536/23; 514/892; 536/1.11
(58) Field of Search ............................. 536/1.11; 514/23, 514/892

(56) References Cited

U.S. PATENT DOCUMENTS

| 4,786,722 | 11/1988 | Zehner ................................. 536/1.1 |
| 5,002,612 | 3/1991 | Beadle et al. ........................ 127/46.1 |
| 5,078,796 | 1/1992 | Beadle et al. ........................ 127/46.1 |
| 5,356,879 | 10/1994 | Zehner et al. ........................ 514/25 |
| 5,447,917 | 9/1995 | Zehner et al. ........................ 514/23 |

OTHER PUBLICATIONS

Kruger et al., Developmental Toxicity of D–Tagatose in Rats, Regul. toxicol. Pharmacol. (1999), 29(2, Pt. 1), S29–S35.*

Levin et al., "Sugar Substitutes: their ernergy values, bulk characteristics, and potential health benefits", Am. J. Clin. Nutr. 1995, vol. 62 (suppl.), pp. 116S–1168S, entire document.

* cited by examiner

Primary Examiner—Howard C. Lee
Assistant Examiner—Everett White
(74) Attorney, Agent, or Firm—Roylance, Abrams, Berdo & Goodman, L.L.P.

(57) ABSTRACT

A method for increasing the fertility of a female mammal comprising administering to said female mammal an efficacious amount of tagatose. A method for promoting healthy fetal development in a pregnant female mammal which comprises administering to said mammal an efficacious amount of tagatose. A method for increasing the birth weight of a fetus in a pregnant female mammal which comprises administering to said mammal an efficacious amount of tagatose. A method for reducing excessive food intake of a pregnant female mammal which comprises administering to said mammal an efficacious amount of tagatose.

18 Claims, No Drawings

INCREASED FERTILITY AND IMPROVED FETAL DEVELOPMENT DRUG

BACKGROUND OF THE INVENTION

This invention relates to the use of tagatose in increasing fertility in mammals, in promoting healthy fetal development in mammals, in increasing the probability for delivering live fetuses in mammals and in controlling food intake during pregnancy of a mammal.

U.S. Pat. No. 4,786,722 discloses edible formulations and methods for preparation of edible formulations in which D-tagatose is used as a low-calorie carbohydrate sweetener and bulking agent. In this patent, D-tagatose is described as useful in foodstuffs and other edible formulations for people whose metabolizable carbohydrate intake must be restricted because of conditions such as diabetes mellitus or obesity.

Safety tests performed on tagatose in its development as a low-calorie sweetener included developmental toxicity studies in rats. Rats are accepted by the US FDA as good models for humans in studying safety and efficacy of food additives and drugs. Newly impregnated rats were placed on various doses of tagatose in their daily diet. Female rats were housed with males nightly in a one-to-one ratio, and each morning inspections for vaginal plugs were made, and in their absence, vaginal smears were taken and tested for sperm. Those females which had been mated were selected for monitoring of fetal development and assigned to tagatose dose groups in a manner so as to provide an equal distribution of mated females among groups and also to equalize the Day 0 gestation mean body weights among the groups. There were 24 mated females in each group. On Days 6–15 of gestation three of the groups received respective total doses of 4,000, 12,000 and 20,000 mg/kg body wt/day administered via gastric intubation in two equally divided doses separated by a four-hour interval. Each dose was administered in 30 ml/kg body weight of distilled, deionized water. Control animals received distilled, deionized water at a comparable volume and frequency. For a period of 20 days following mating, the rats were observed and measurements taken daily. Upon the $20^{th}$ day, the rats were killed and a wide variety of physical, toxicological, and fetal developmental parameters was determined for treatment effects. No adverse effects in the dams or fetuses were found. However, I noted unpredictable, novel and beneficial effects with respect to fertility and fetal development.

Table 1 presents the reproductive performance of the test and control groups of rats. It is seen that the numbers of females impregnated was 83.3% for the rats receiving no tagatose, and 100%, 91.3% and 100%, respectively for the rats receiving 4,000, 12,000 and 20,000 mg/kg body wt/day. Since each of the rats was selected after mating, with, therefore, equal chance of becoming pregnant, it is evident that the administration of tagatose on the $6^{th}$ through $15^{th}$ days after mating resulted in greater numbers of pregnancies.

TABLE 1

Reproductive Performance of Female Crl:CD (SD) BR Rats Fed D-Tagatose from Days 6 to 15 of Gestation

| | Dose levels of D-Tagatose (in mg/kg/day) | | | |
|---|---|---|---|---|
| | 0 | 4,000 | 12,000 | 20,000 |
| Number of females placed with males | 24 | 23[a] | 23[a] | 24 |
| Number of females pregnant (%)[b] | 20 (83.3%) | 23 (100%) | 21 (91.3%) | 24 (100%) |
| Fertility index | 83.3 | 100 | 91.3 | 100 |
| Number of females bearing viable fetuses | 20 | 23 | 21 | 24 |
| Number of *corpora lutea*[c] | 17.8 ± 3.0 | 17.7 ± 2.8 | 17.7 ± 2.9 | 17.4 ± 2.8 |
| Number of implantation sites[c] | 15.3 ± 3.2 | 16.5 ± 2.3 | 15.9 ± 2.9 | 15.3 ± 2.9 |
| Preimplantation loss[c,d] | 0.129 ± 0.183 | 0.053 ± 0.113 | 0.094 ± 0.151 | 0.107 ± 0.162 |
| Number of resorptions[c] | 1.0 ± 1.2 | 1.1 ± 0.9 | 0.5 ± 0.9 | 0.8 ± 0.8 |
| Postimplantation loss[c,e] | 0.059 ± 0.071 | 0.068 ± 0.051 | 0.043 ± 0.087 | 0.047 ± 0.049 |
| Number of litters with resorptions(%)[b] | 12 (60.0%) | 18 (78.3%) | 6 (28.6%) | 13 (54.2%) |
| Total number of viable fetuses | 287 | 354 | 322 | 350 |
| Number of males fetuses[c] | 6.9 ± 2.0 | 7.4 ± 2.3 | 7.8 ± 2.3 | 7.5 ± 2.3 |
| Number of female fetuses[c] | 7.5 ± 2.5 | 8.0 ± 2.2 | 7.5 ± 2.2 | 7.1 ± 2.3 |
| Number of dead fetuses | 0 | 0 | 0 | 0 |
| Body weight (g) of viable fetuses[c] | 3.47 ± 0.28 | 3.56 ± 0.21 | 3.75 ± 0.32** | 3.57 ± 0.24 |
| Male fetuses[c] | 3.58 ± 0.27 | 3.64 ± 0.22 | 3.84 ± 0.33* | 3.68 ± 0.27 |
| Female fetuses[c] | 3.37 ± 0.27 | 3.49 ± 0.20 | 3.65 ± 0.35** | 3.49 ± 0.19 |

[a] Excludes data from one female that delivered prior to Day 20. On the basis of the weight of the delivered pups, pregnancy appeared to be greater than Day 20 gestation.
[b] N (%), total number affected (percentage of total number evaluated).
[c] Values are means ± SD.
[d] Preimplantation loss = (*corpora lutea*-implants)/(*corpora lutea*).
[e] Postimplantation loss = (resorptions/implantations).
*Difference from control statistically significant ($P \leq 0.05$).
**Difference from control statistically significant ($P \leq 0.01$).

Table 1 also shows that, of the impregnated rats, each in those groups receiving tagatose produced greater numbers of live fetuses than those not given tagatose. Thus tagatose not only increased the numbers of pregnancies, but also was responsible for greater numbers of fetuses maintained alive up to the date of sacrifice. Total numbers of live fetuses were 354, 322 and 350 for the groups receiving 4,000, 12,000 and 20,000 mg/kg body wt/day, respectively, versus 287 live fetuses for the control group. Thus, tagatose administered six through 15 days after mating resulted in a greater number of live fetuses at Day 20 than in rats not receiving tagatose.

It is commonly known that underweight fetuses are subject to increased risks of disease and many forms of growth and developmental problems in utero and after birth. Table 1 shows that the fetuses of each group of rats on tagatose weighed more than the fetuses of the control rats. It is seen that this was true for the total numbers of fetuses as well as for males and females separately. Furthermore, fetuses from rats on tagatose were within the normal weight range for their ages: 3.35–3.86 g for males and 3.19–3.63 g for females.

One of the common problems associated with pregnancy is overeating which can result in excess weight gain with its concomitant health risks to the mother and fetus. As seen in Table 2, during the rats' period on tagatose, Day 6 through Day 15, their total daily food intakes were less than the daily food intakes of rats in the control group. This represents a clear health advantage for both dam and fetus receiving tagatose. That tagatose was responsible is seen by the fact that Table 2 shows that food intakes for the test and control groups were essentially the same from Day 0 to Day 6, when tagatose administration began, and that food intakes for the test rats increased after they were taken off tagatose, beginning Day 16. In this rat study, no consistent weight loss in the dams accompanied the reduction in intakes (except for the period from Day 6 to Day 9 attributed to taxation in the high tagatose dose groups).

TABLE 2

Food Consumption in Female Crl: CD(SD)BR Rats Fed D-Tagatose during Pretreatment (Days 0 to 6 of Gestation), Treatment (Days 6 to 15 of Gestation), and Posttreatment (Days 16–20 of Gestation)

| | Dose levels of D-tagatose (in mg/kg/day) | | | |
|---|---|---|---|---|
| Days of pregnancy | 0 | 4,000 | 12,000 | 20,000 |
| Number of dams/group | 20 | 23 | 21 | 24 |
| Food intake (g/kg body wt/day)$^a$ | | | | |
| Days 0–6 | 104 ± 11 | 103 ± 7 | 104 ± 8 | 107 ± 9 |
| Days 6–9 | 93 ± 7 | 84 ± 4 | 69 ± 7** | 51 ± 4** |
| Days 9–12 | 93 ± 5 | 91 ± 5 | 84 ± 5** | 80 ± 7** |
| Days 12–16 | 89 ± 4 | 90 ± 5 | 83 ± 5** | 77 ± 6** |
| Days 16–20 | 90 ± 4 | 94 ± 3 | 99 ± 5** | 102 ± 6** |
| Food intake (g/animal)$^a$ | | | | |
| Days 0–6 | 145 ± 17 | 144 ± 11 | 148 ± 8 | 149 ± 14 |
| Days 6–9 | 77 ± 8 | 70 ± 5 | 58 ± 6** | 43 ± 12** |
| Days 9–12 | 80 ± 6 | 78 ± 7 | 73 ± 6** | 67 ± 7** |
| Days 12–16 | 109 ± 8 | 112 ± 9 | 105 ± 9** | 94 ± 10** |
| Days 16–20 | 121 ± 9 | 129 ± 10** | 137 ± 9** | 138 ± 11** |

$^a$Values are means ± SD.
*Difference from control statistically significant ($P \leq 0.05$).
** Difference from control statistically significant ($P \leq 0.01$).

SUMMARY OF THE INVENTION

In accordance with one aspect of this invention, there is provided a method for increasing the fertility of a female mammal, especially a human female which comprises administering to said mammal an efficacious amount of tagatose, preferably D-tagatose.

In accordance with another aspect of this invention, there is provided a method for promoting healthy fetal development in a pregnant female mammal, especially a pregnant human female, which comprises administering to said mammal an efficacious amount of tagatose, preferably D-tagatose, during pregnancy.

According to another aspect of this invention, there is provided a method for increasing the birth weight of a fetus in a pregnant female mammal, especially a pregnant human female, which comprises administering to said mammal an efficacious amount of tagatose, preferably D-tagatose.

According to another aspect of this invention, there is provided a method for reducing excessive food intake of a pregnant female mammal, especially a pregnant human female, which comprises administering to said mammal an efficacious amount of tagatose, preferably D-tagatose.

DETAILED DESCRIPTION OF THE INVENTION

The tagatose may be administered to a mammal subject in combination with a food, beverage or taken separately in powder, crystalline or liquid form. As diluent, if needed, one may use liquid or solid carriers, such as water, starch, alcohol, or other non-toxic substances. Preferably, the tagatose is administered within the range of 100–2000 mg/kg body weight/day. The tagatose may be administered daily, every other day or at other prescribed frequencies. The tagatose may be D-tagatose, L-tagatose or a mixture thereof.

EXAMPLE 1

Increased Fertility

A 70 kg human female with a history of difficulty in conceiving begins taking tagatose twice daily at five g per dose, beginning one month before an attempt to conceive. She finds that her attempt is successful and she is pregnant.

EXAMPLE 2

Increased Probability of Live Birth

A 70 kg human female with a history of spontaneous abortions and stillbirths takes tagatose twice daily at five g per dose, beginning one month before an attempt to conceive. She becomes pregnant, and the pregnancy proceeds to a successful conclusion, delivering a live birth.

EXAMPLE 3

Increased Birth Weight

A 70 kg human female takes precautions against giving birth to a below average weight infant by taking tagatose twice daily at five g per dose, beginning one month before an attempt to conceive. She becomes pregnant and delivers a baby within the normal birth weight range despite a family history of frequent low birth weight babies.

EXAMPLE 4

Reduced Food Intake

A 70 kg human female inclined toward obesity desires a child, but is concerned that pregnancy may increase her food intake causing weight problems as experienced in her past pregnancies. She takes tagatose twice daily at five g per dose, beginning one month before an attempt to conceive. She becomes pregnant, but her average daily diet does not increase, and her weight gain is within the range advised by her physician. She delivers a healthy, normal child.

What is claimed is:

1. A method for increasing the fertility of a female mammal comprising administering to said female mammal an efficacious amount of tagatose.

2. The method of claim 1 wherein the mammal is a human.

3. The method of claim 1 wherein said efficacious amount is from 100–2000 mg/kg body weight/day is administered to said mammal.

4. The method of claim 1 wherein the prescribed dose is taken every day.

5. The method of claim 1 wherein the prescribed dose is taken every other day.

6. The method of claim 1 wherein said tagatose is D-tagatose, L-tagatose or a mixture thereof.

7. The method of claim 1 wherein said tagatose is D-tagatose, L-tagatose or a mixture thereof.

8. A method for promoting healthy fetal development in a pregnant female mammal which comprises administering to said mammal an efficacious amount of tagatose.

9. The method of claim 8 wherein the mammal is a human.

10. The method of claim 8 wherein said efficacious amount is from 100–2000 mg/kg body weight/day is administered to said mammal.

11. The method of claim 8 wherein the prescribed dose is taken every day.

12. The method of claim 8 wherein the prescribed dose is taken every other day.

13. A method for increasing the birth weight of a fetus in a pregnant female mammal which comprises administering to said mammal an efficacious amount of tagatose.

14. The method of claim 13 wherein the mammal is a human.

15. The method of claim 13 wherein said efficacious amount is from 100–2000 mg/kg body weight/day is administered to said mammal.

16. The method of claim 13 wherein the prescribed dose is taken every day.

17. The method of claim 13 wherein the prescribed dose is taken every other day.

18. The method of claim 13 wherein said tagatose is D-tagatose, L-tagatose or a mixture thereof.

* * * * *